(12) United States Patent
Rybyanets

(10) Patent No.: US 8,568,339 B2
(45) Date of Patent: Oct. 29, 2013

(54) SINGLE ELEMENT ULTRASOUND TRANSDUCER WITH MULTIPLE DRIVING CIRCUITS

(75) Inventor: Andrey Rybyanets, Yoqneam (IL)

(73) Assignee: UltraShape Ltd., Yoknean Illit (IL)

( * ) Notice: Subject to any disclaimer, the term of this patent is extended or adjusted under 35 U.S.C. 154(b) by 743 days.

(21) Appl. No.: 11/889,828

(22) Filed: Aug. 16, 2007

(65) Prior Publication Data

US 2009/0048544 A1 Feb. 19, 2009

(51) Int. Cl.
*A61H 1/00* (2006.01)
(52) U.S. Cl.
USPC .............................................. 601/2
(58) Field of Classification Search
USPC .................. 600/437, 459; 601/2, 4; 604/22; 367/138, 155, 157
See application file for complete search history.

(56) References Cited

U.S. PATENT DOCUMENTS

| | | | |
|---|---|---|---|
| 4,972,839 A | 11/1990 | Angelsen | |
| 5,267,985 A | 12/1993 | Shimada et al. | |
| 5,523,058 A * | 6/1996 | Umemura et al. | 422/128 |
| 6,071,239 A | 6/2000 | Cribbs et al. | |
| 6,181,052 B1 * | 1/2001 | Puskas | 310/325 |
| 6,312,383 B1 | 11/2001 | Lizzi et al. | |
| 6,635,017 B1 | 10/2003 | Moehring et al. | |
| 7,914,469 B2 * | 3/2011 | Torbati | 601/2 |
| 2003/0083536 A1 | 5/2003 | Eshel et al. | |
| 2004/0039312 A1 * | 2/2004 | Hillstead et al. | 601/2 |
| 2005/0154314 A1 | 7/2005 | Quistgaard | |
| 2005/0249667 A1 | 11/2005 | Tuszynski et al. | |
| 2006/0169029 A1 | 8/2006 | Heyman | |

OTHER PUBLICATIONS

He, P Z, et al, "Dual-Frequency High Intensity Focused Ultrasound (HIFU) Accelerating Therapy", Proceedings of the IEEE Engineering in Medicine and Biology Society, $27^{th}$ Annual Conference, Shanghai, China, Sep. 1-4, 2005, pp. 213-216.
Iernetti, et al, "Enhancement of High-Frequency Cavitation Effects by a Low Frequency Stimulation", Ultrasonics Sonochemistry 4, 1997, pp. 263-268.
Cooper, et al, "Controlled Ultrasound Tissue Erosion: the Effects of Tissue Type, Exposure Parameters and the Role of Dynamic Microbubble Activity", IEEE International Ultrasonics, Ferroelectrics, and Frequency Control Joint $50^{th}$ Anniversary Conference, 2004, pp. 1808-1811.
Zhen, et al, "Optical and acoustic monitoring of bubble cloud dynamics at a tissue-fluid interface in ultrasound tissue erosion", Journal Acoustical Society of America, 121 (4), Apr. 2007, pp. 2421-2430.
Pei, et al, "The affection on the tissue lesions of difference frequency in dual-frequency high-intensity ultrasound (HIFU)", Ultrasonics Sonochemistry, XXX, 2005, in press, pp. 1-6.
Feng, et al, "Enhancement of ultrasonic cavitation yield by multi-frequency sonication", Ultrasonics Sonochemistry 9, 2002, pp. 231-236.

* cited by examiner

*Primary Examiner* — Parikha Mehta
(74) *Attorney, Agent, or Firm* — Edward J. Stemberger; Manelli Selter PLLC

(57) ABSTRACT

Apparatus for generating high intensity acoustic beams, the apparatus comprising: a piezoelectric transducer characterized by a plurality of harmonic resonant frequencies of vibration; and at least one driving circuit connected to the transducer that is controllable to excite at least two vibrations of the transducer at different harmonic vibration frequencies of the vibrator, which vibrations generate a high intensity acoustic beam for each of the harmonic frequencies.

15 Claims, 4 Drawing Sheets

SINGLE ELEMENT ULTRASOUND TRANSDUCER WITH MULTIPLE DRIVING CIRCUITS

FIELD OF THE INVENTION

The invention relates to methods and apparatus for performing acoustic procedures on tissue.

BACKGROUND OF THE INVENTION

Various methods are known for delivering and coupling acoustic energy to a region of tissue to perform diagnostic and/or therapeutic and/or cosmetic procedures on a patient's tissue. Among such procedures are for example, non-invasive assaying of blood analytes, drug delivery by phonophoresis, lithotripsy, tissue ablation and lysis of fat cells for cosmetic removal of adipose tissue.

U.S. Pat. No. 5,267,985 describes "diffusion of a substance to a local area of material or tissue by providing ultrasonic energy to the substance and material in two or more distinct frequencies simultaneously. Each of the distinct frequencies of ultrasonic energy is chosen to enhance permeability of the substance through one or more diffusion rate-limiting sections of the material." The patent notes that the intensities of the different frequencies of ultrasound "typically do not coincide and, as a result, the use of a multiple frequency system can provide a more uniform axial intensity over a greater distance than can a single frequency ultrasound system." In an embodiment of the invention, the acoustic energy is produced by "driving a single transducer with voltage corresponding to the sum of voltages required to produce each frequency desired".

For many types of therapeutic and/or cosmetic acoustic applications, such as for example lithotripsy, tissue ablation and lysis noted above, sufficient acoustic energy must be delivered to a tissue region to destroy and remove tissue in the region. Generally, the acoustic energy is delivered by focusing at least one beam of relatively intense ultrasound on the region. The high intensity, focused ultrasound, conventionally referred to by the acronym "HIFU", generates thermal stress and/or cavitation that disrupts and destroys the tissue. Tissue raised to and maintained at a temperature above about 42° C. rapidly dies and mechanical stresses generated by cavitation breach and tear cell membranes of the tissue.

Various studies have indicated that efficacy of destruction and removal of tissue from a tissue region using high intensity ultrasound can generally be enhanced by applying more than one frequency of ultrasound to the region. Typically, the ultrasound is applied to the region by generating two beams of different frequency ultrasound using separate transducers and driving circuits and focusing the beams on the region.

P. Z. He et al in "Dual-Frequency High Intensity Focused Ultrasound (HIFU) Accelerating Therapy"; Proceedings of the IEEE Engineering in Medicine and Biology, 27th Annual Conference, Shanghai, China; Sep. 1-4, 2005; pp 213-216, concluded from "preliminary experimental results" that "dual frequency HIFU induces larger lesion in tissue than conventional single frequency HIFU under the same exposure conditions". The dual frequency experiments were carried out by irradiating tissue regions, apparently simultaneously, with ultrasound at 1.563 MHz and 1.573 MHz radiated by central disc and confocal annulus PZT-4 transducers respectively. G. Iernetti et al in "Enhancement of high-frequency cavitation effects by a low frequency stimulation", Ultrasonics Sonochemistry 4 (1997) pp 263-268, describe enhancing cavitation effects in tissue generated by relatively high frequency ultrasound at 700 kHz using relatively low frequency ultrasound at 20 kHz. The low frequency ultrasound was used to generate a "stimulating field" that was applied to a tissue region to amplify cavitation effects of the high frequency ultrasound at different stages of cavitation in the tissue region caused by the high frequency ultrasound.

All the above referenced documents are incorporated herein by reference.

SUMMARY OF THE INVENTION

An aspect of some embodiments of the invention, relates to providing apparatus to generate acoustic beams at least two different frequencies for treating tissue such as for lysing and/or removal of tissue in a tissue region. Optionally, the frequencies are ultrasound frequencies. Optionally, the tissue region comprises adipose tissue.

According to an aspect of some embodiments of the invention, the at least two frequencies are resonant vibration frequencies of each of a same at least one piezoelectric element. In an embodiment of the invention, the resonant frequencies are odd harmonic frequencies of the element. Optionally, the at least one same piezoelectric element comprises a single piezoelectric element.

In some embodiments of the invention, a same driving circuit is used to excite vibrations at each of the at least two frequencies in an element of the same at least one piezoelectric element. In some embodiments of the invention, a plurality of driving circuits is used to excite vibrations at each of the at least two frequencies in an element of the same at least one piezoelectric element.

In an embodiment of the invention, the driving circuit is controllable to excite different configurations of vibrations in the piezoelectric element at the at least two resonant frequencies and provide thereby different configurations of acoustic beams for illuminating tissue region.

In some embodiments of the invention, the driving circuit is controlled to excite the piezoelectric element to generate beams at different resonant frequencies of the piezoelectric element that simultaneously illuminate the region. In some embodiments of the invention, the driving circuit is controlled to generate beams to sequentially illuminate the region with acoustic energy at different resonant frequencies of the piezoelectric element. In some embodiments of the invention, the driving circuit is controlled to provide different relative intensities of beams at different frequencies.

For convenience of presentation, ultrasonic energy radiated by the piezoelectric element at each resonant frequency is referred to as a "beam" of ultrasonic energy, irrespective of whether the element radiates the energy with or without simultaneously radiating energy at another resonant frequency.

In some embodiments of the invention, the beams are spatially and/or temporally configured to interact and provide enhanced cavitation of tissue. Optionally, the cavitation is inertial cavitation, also referred to as unstable cavitation. Optionally, the cavitation is non-inertial cavitation, also referred to as stable cavitation. Inertial cavitation refers to cavitation in which a void or bubble in a material rapidly collapses, producing a shock wave and a relatively "violent" release of energy. Non-inertial cavitation refers to cavitation in which a bubble in a material is forced to oscillate in size or shape as a result of being subject to forces generated by an input of energy, for example as may be provided by an acoustic field. Optionally, the beams are configured to provide non-cavitation mechanical stress, optionally shear stress and/ or thermal gradients advantageous for treating tissue in the tissue region. For example, the beams may be configured to generate stress advantageous for increasing blood flow to and/or for activation of macrophages in the region.

There is therefore provided in accordance with an embodiment of the invention, Apparatus for generating high intensity acoustic beams, the apparatus comprising: a piezoelectric transducer characterized by a plurality of harmonic resonant frequencies of vibration; and at least one driving circuit connected to the transducer that is controllable to excite at least two vibrations of the transducer at different harmonic vibration frequencies of the vibrator, which vibrations generate a high intensity acoustic beam for each of the harmonic frequencies.

Optionally the apparatus comprises a controller that selectively controls the at least one drive circuit to simultaneously excite vibrations of the transducer at least two harmonic frequencies or to excite vibrations at different harmonic frequencies at different times. Additionally or alternatively, the transducer is configured so that the beams share a region in which they overlap. Optionally, the transducer is a focusing transducer. In some embodiments of the invention, the transducer is a non-focusing transducer.

In some embodiments of the invention, the piezoelectric transducer is a component transducer of a multi-element transducer comprising a plurality of component transducers controllable to generate high intensity acoustic beams.

In some embodiments of the invention, at least one of the beams is suitable for causing cavitation in biological tissue located at the overlap region. Optionally, the cavitation comprises inertial cavitation. Additionally or alternatively, the cavitation comprises non-inertial cavitation.

In some embodiments of the invention, at least one of the beams is configured to enhance cavitation in the overlap region.

In some embodiments of the invention, at least one of the beams is suitable for generating thermal stress in biological tissue located at the overlap region. Optionally, the beams are configured so that the thermal stress destroys tissue in the overlap region.

In some embodiments of the invention, at least one of the beams is suitable for generating thermal gradients in biological tissue located at the overlap region.

In some embodiments of the invention, at least one of the beams is suitable for generating mechanical stress in biological tissue located at the overlap region. Optionally, the mechanical stress comprises shear stress. Additionally or alternatively, the beams are configured so that the mechanical stress destroys tissue in the overlap region.

In some embodiments of the invention, the tissue comprises adipose tissue.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION

Figure 1A:
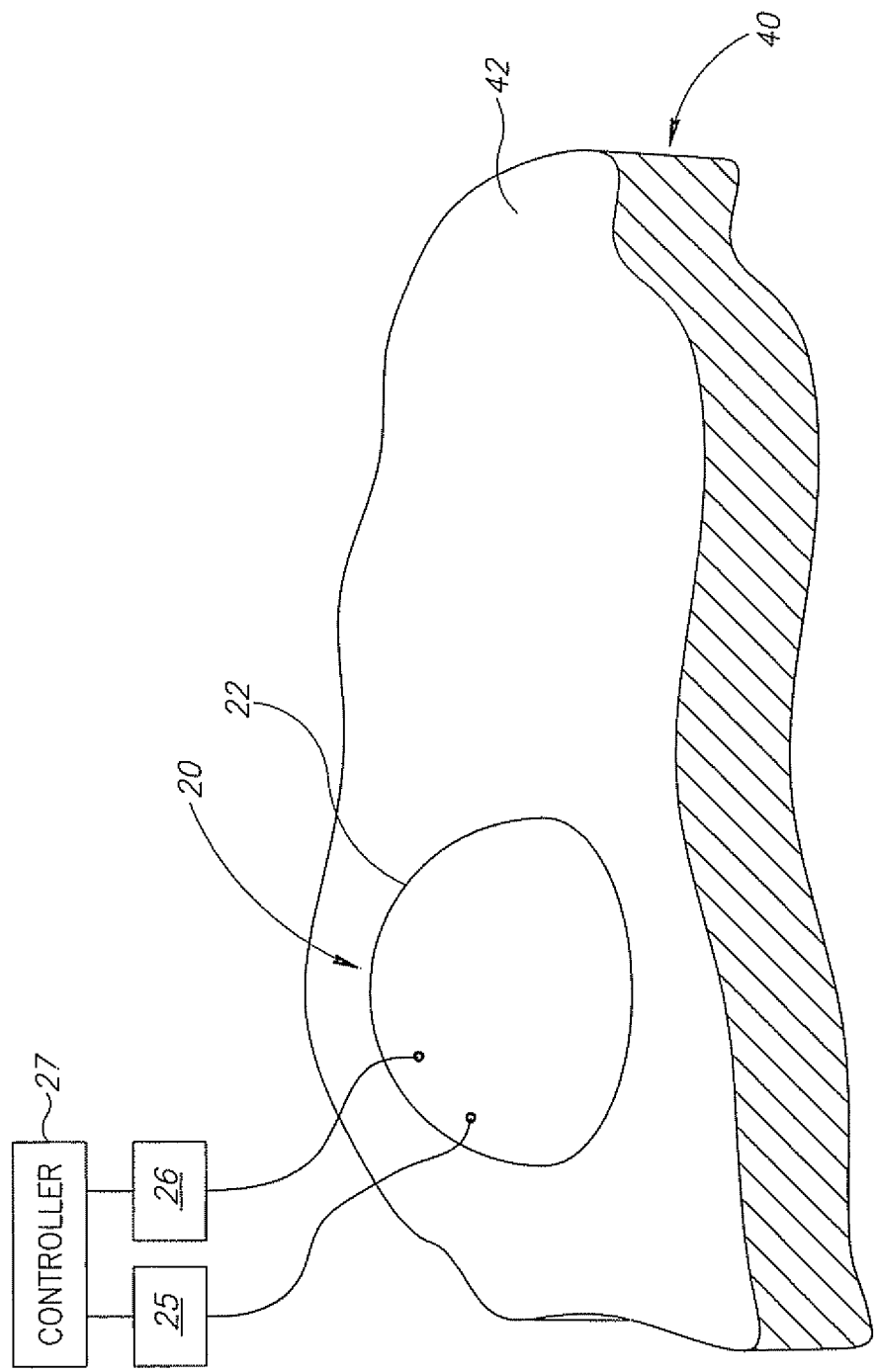
FIGS. 1A and 1B schematically show perspective and cross section views respectively of a single element spherical focusing piezoelectric transducer and driving circuit being used to lyse adipose tissue, in accordance with an embodiment of the invention.
Figure 1B:
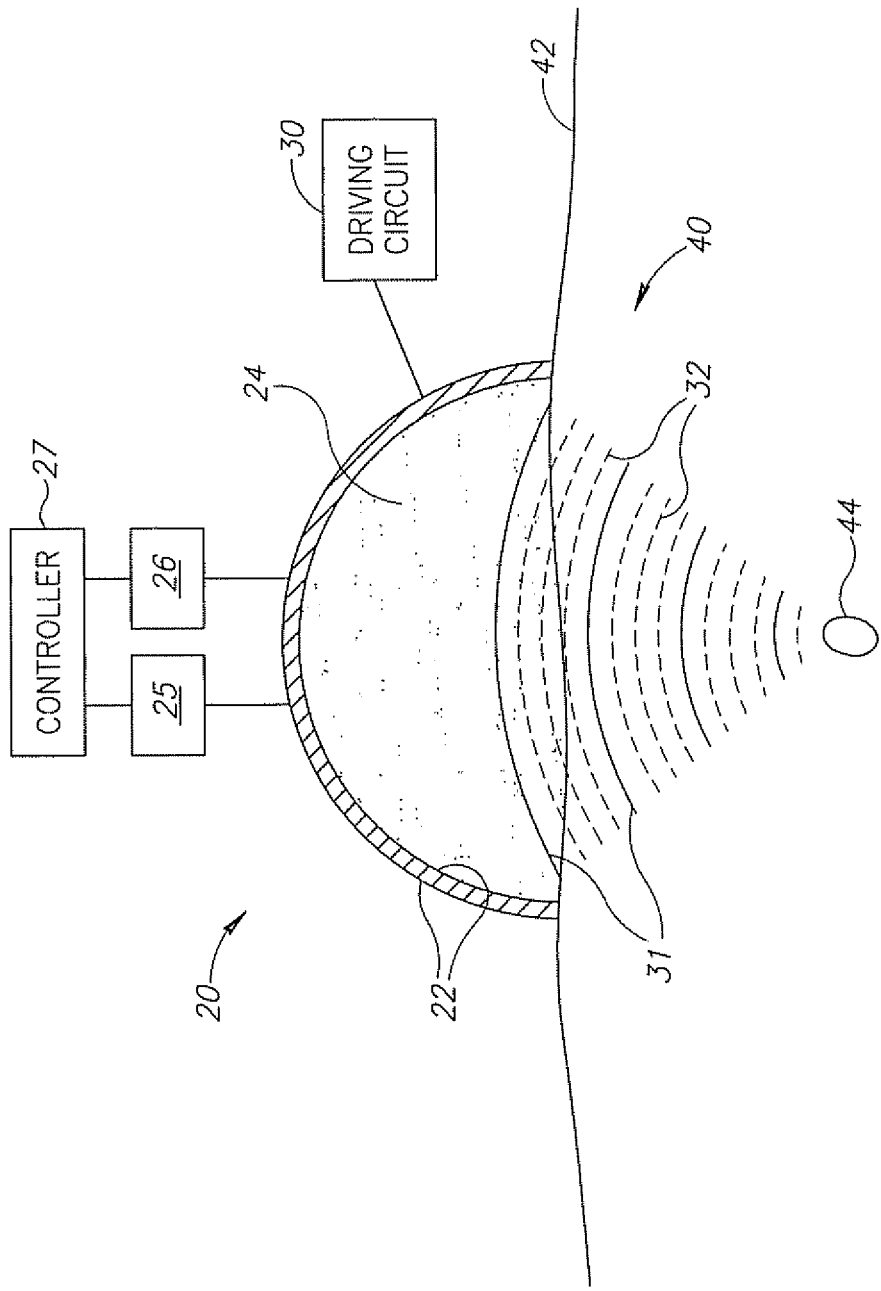

FIGS. 1A and 1B schematically show perspective and cross section views respectively of a single element spherical focusing piezoelectric transducer 20 being used, by way of example to provide high intensity focused ultrasound (HIFU) to lyse adipose tissue in a tissue region 40 of a patient's body below the patient's skin 42, in accordance with an embodiment of the invention. Transducer 20 may be produced using any of various methods and devices known in the art and is formed having electrodes (not shown) optionally on its surfaces 22 that are electrifiable to excite vibrations in the transducer that generate, optionally, ultrasonic beams. Transducer 20 is optionally filled with a suitable coupling gel 24 (FIG. 1B) for acoustically coupling the transducer to the patient's skin.

Transducer 20 is coupled to at least one driving circuit controlled by a suitable controller to electrify the transducer to excite resonant vibration modes of the transducer and generate relatively high intensity ultrasound waves for lysing adipose tissue. By way of example, in FIG. 1B transducer 20 is coupled to two driving circuits, a driving circuit 25 and a driving circuit 26. In accordance with an embodiment of the invention, driving circuits 25 and 26 are controlled by a controller 27 to excite vibration modes of transducer 20 at least two different, odd harmonic resonant vibration frequencies of the transducer for which mass points in the transducer vibrate along directions substantially perpendicular to surfaces 22.

It is noted that to generate the ultrasound beams, surfaces 22 of transducer 20 are required to be free to vibrate along directions perpendicular to the surfaces, and that therefore surfaces 22 are located substantially at antinodes of "perpendicular" vibration modes of transducer 20. As a result, substantially only odd harmonic perpendicular resonant vibrations are excitable in the transducer.

Each odd harmonic resonant vibration generates an ultrasound beam substantially at the corresponding resonant frequency of the resonant vibration, which ultrasound beam is optionally focused by transducer 20 to a focal region 44 in tissue region 40, at which focal region adipose tissue is lysed. Optionally, driving circuit 25 operates to excite transducer 20 at a first harmonic resonant vibration mode of the transducer and driving circuit 26 operates to excite the transducer at a third harmonic resonant vibration mode of the transducer.

By way of example, FIG. 1B schematically shows driving circuits 25 and 26 controlled by controller 27 to simultaneously electrify electrodes comprised in transducer 20 to generate two HIFU ultrasound beams, schematically represented by solid and dashed wave fronts 31 and 32 respectively. The ultrasound waves are focused to, and at least partially overlap, in a focal region 44 indicated by a dashed perimeter in tissue region 40. Dashed wave fronts of ultrasound beam 32 are shown having a smaller pitch than solid wave fronts of ultrasound beam 31 to indicate that ultrasound beam 32 is characterized by a higher frequency than ultrasound beam 31. Optionally, as noted above, ultrasound beams 31 and 32 are generated by first and third harmonic resonant vibrations of transducer 20.

By way of a numerical example, in some embodiments of the invention, transducer 20 is formed from a material and having dimensions so that it has first and third harmonic resonant vibrations at frequencies of about 200 kHz and about 680 kHz respectively. The third resonant harmonic vibration frequency is not an exact multiple of three times the first resonant harmonic vibration frequency because, generally, for piezoelectric materials electromechanical coupling of an electrical field that excites the harmonic vibrations to the piezoelectric material shifts the harmonic frequencies.

Whereas in FIG. 1B and the description above controller 27 is indicated as controlling driving circuits 25 and 26 to simultaneously generate beams 31 and 32, practice of the invention is not limited to simultaneously exciting harmonic resonant frequency acoustic beams. Beams such as beams 31 and 32 may be generated in any configuration suitable for performing a HIFU medical or cosmetic procedure. For example, for lysing tissue in region 44 optionally beams 31 and 32 are generated to sequentially illuminate region 44 with pulses of acoustic energy.

In an embodiment of the invention, lower frequency beam 31 may be generated to illuminate region 44 following a delay time after the region is illuminated by ultrasound beam 32, which delay is determined so that beam 31 enhances cavitation in the region caused by beam 32. Optionally, the delay time is determined responsive to a relaxation time that characterizes decrease in a number of micro-bubbles formed in region 44 by acoustic energy from beam 32. Acoustic energy from beam 31 optionally operates to slow the rate of decrease in the number of micro-bubbles. Optionally the delay time is determined responsive to a tissue relaxation time or a resonance frequency of tissue components. Other protocols for configuring and using ultrasound beams in accordance with an embodiment of the invention, such as beams 31 and 32, will occur to a person of the art.

Piezoelectric transducer 20 may be modeled for proposes of determining its response to voltage provided by driving circuits 25 and 26 by any of various equivalent circuits known in the art. Generally, an equivalent circuit for modeling a piezoelectric transducer comprises a plurality of RLC sub-circuits, each having a resonant frequency at a different one of the resonant vibration frequencies of the transducer.

Figure 2A:
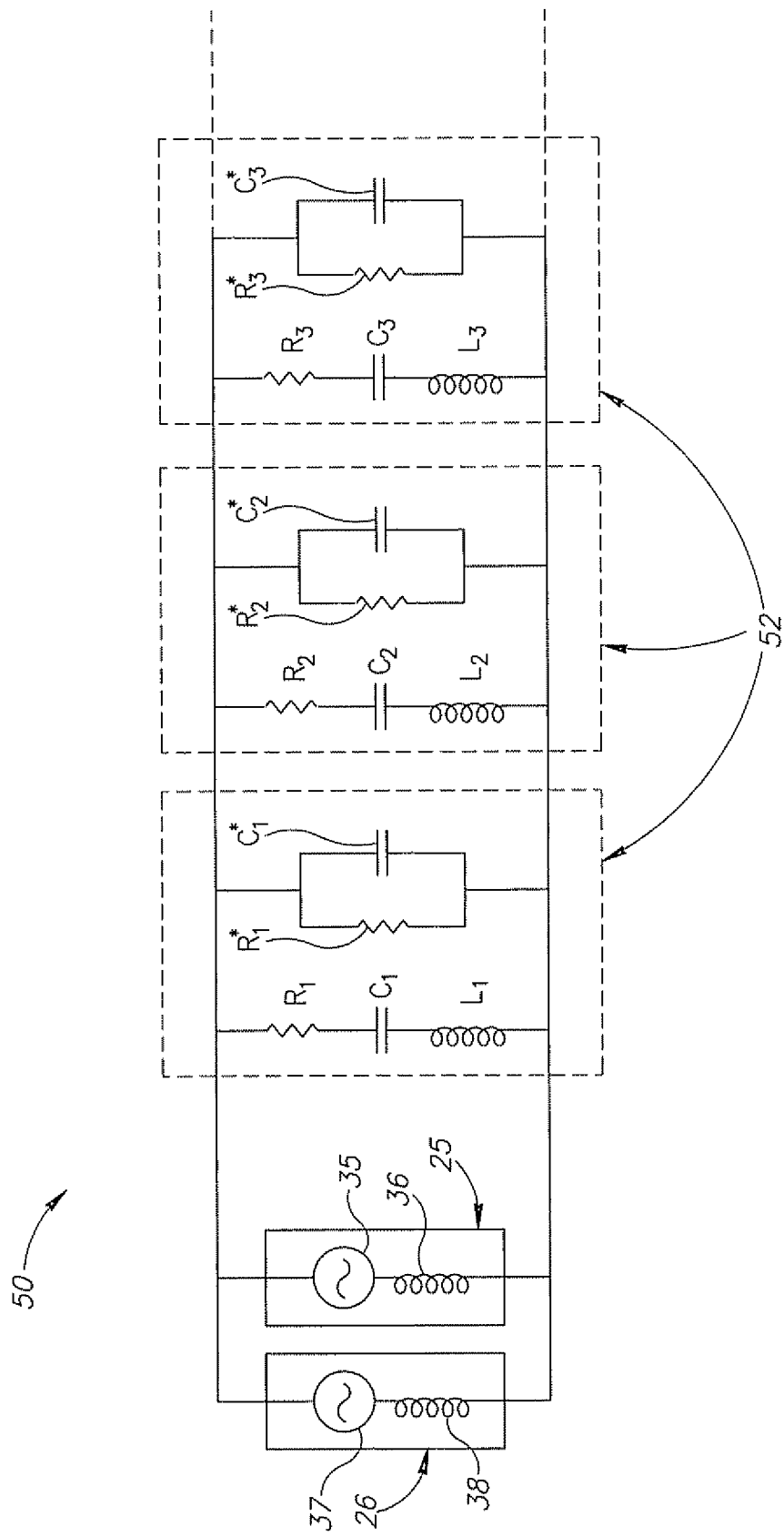
FIG. 2A schematically shows an equivalent circuit model of the piezoeletric transducer shown in FIGS. 1A and 1B.
Figure 2B:
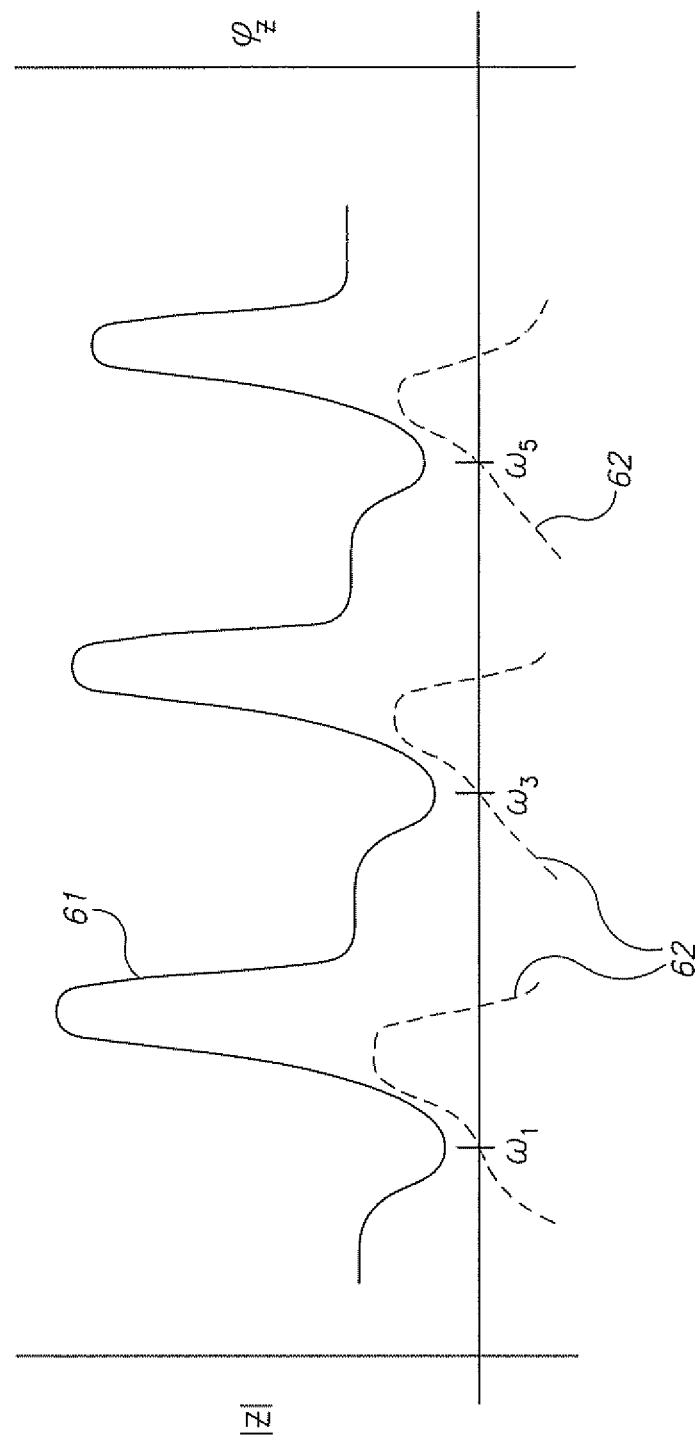
FIG. 2B shows a graph of magnitude and phase of impedance of the equivalent circuit shown in FIG. 2A as a function of frequency of voltage electrifying the transducer.

FIG. 2A schematically shows an equivalent circuit 50 for modeling transducer 20 comprising a plurality of Van Dyke RLC sub-circuits, each delineated by a dashed rectangle 52 and having a resonant frequency at a different odd harmonic resonant vibration frequency of the transducer. For convenience of presentation, equivalent circuit 50 comprises only three sub-circuits 52, which are assumed to have resonant frequencies at the first three odd resonant vibration frequencies of transducer 20. FIG. 2B shows a graph 60 having a schematic solid curve 61 that represents the magnitude of impedance of equivalent circuit 50 as a function of frequency of voltage applied to transducer 20. The minima of curve 61 occur substantially at the odd harmonic resonant frequencies of transducer 20 and the equivalent circuit, which frequencies are indicated along the abscissa as $\omega_1$, $\omega_3$ and $\omega_5$. Magnitude of the impedance in arbitrary units is indicated along an ordinate of graph 60 at a left side of the graph. A portion of a dashed curve 62 crosses the abscissa at each resonant frequency $\omega_1$, $\omega_3$ and $\omega_5$ and schematically represents the phase of the impedance near the resonant frequency. Magnitude of the phase in arbitrary units is indicated along an ordinate of graph 60 at the right side of the graph.

Driving circuit 25 shown in FIGS. 1A and 1B is schematically shown in FIG. 2A comprising a power supply 35 connected in series with a matching inductor 36 to equivalent circuit 50. Matching inductor 36 has an inductance that matches driving circuit 25 to the equivalent circuit (and thereby to transducer 20) so that power provided by the driving circuit is absorbed preferably by sub-circuit 52 characterized by the first resonant frequency $\omega_1$ of transducer 20. Driving circuit 26 shown in FIGS. 1A and 1B is optionally similar to driving circuit 25 and is shown in FIG. 2A comprising a power supply 37 and matching inductor 38 connected to equivalent circuit 50. Matching inductor 38 has an inductance that matches driving circuit 25 to the equivalent circuit, and thereby to transducer 20, so that power provided by the driving circuit is absorbed preferably by sub-circuit 52 characterized by the third harmonic resonant frequency $\omega_3$ of transducer 20.

It is noted that, whereas transducer 20 is described as being used to lyse adipose tissue, a transducer similar to transducer 20 and associated driving and control circuitry in accordance with an embodiment of the invention, may be used to generate HIFU for other procedures. For example a transducer and circuitry in accordance with an embodiment of the of the invention, similar to that shown in FIGS. 1A and 1B may be used to perform lithotripsy or ablation of cardiac or liver tissue.

Practice of the invention is of course not limited to a focusing transducer such as transducer 20, but may be practiced with focusing transducers different from transducer 20 and/or with non-focusing transducers, such as a planar transducer. Furthermore, in some embodiments of the invention a transducer may be coupled to a single driving circuit that excites the transducer to generate high intensity acoustic beams at a plurality of different harmonic resonant vibration frequencies. It is also noted that whereas transducer 20 is shown as a single element transducer, a transducer in accordance with an embodiment of the invention may be a multi-element transducer comprising a plurality of component transducers. At least one of the component transducers of the multi-element transducer is excited at least two odd harmonic resonant vibration frequencies of the component element to provide ultrasound beams suitable for treating tissue.

In the description and claims of the present application, each of the verbs, "comprise" "include" and "have", and conjugates thereof, are used to indicate that the object or objects of the verb are not necessarily an exhaustive listing of members, components, elements or parts of the subject or subjects of the verb.

The invention has been described with reference to embodiments thereof that are provided by way of example and are not intended to limit the scope of the invention. The described embodiments comprise different features, not all of which are required in all embodiments of the invention. Some embodiments of the invention utilize only some of the features or possible combinations of the features. Variations of embodiments of the described invention and embodiments of the invention comprising different combinations of features than those noted in the described embodiments will occur to persons of the art. The scope of the invention is limited only by the following claims.

The invention claimed is:

1. An apparatus for lysing adipose tissue, the apparatus comprising:
   a controller;
   at least two driving circuits; and
   a single element focusing piezoelectric transducer, wherein the controller and focusing piezoelectric transducer are connected to the at least two driving circuits and the controller is configured to selectively control the at least two driving circuits, such that the transducer is excited at a plurality of odd harmonic resonant frequencies of vibration, thereby emitting a plurality of ultrasonic beams that at least partially overlap at a focal region in the adipose tissue, and wherein at least one ultrasonic beam of the plurality of ultrasonic beams induces cavitation in the adipose tissue at the focal region and a different ultrasonic beam slows down the rate of decrease in the amount of cavitation.

2. The apparatus according to claim 1, wherein said transducer is a component transducer of a multi-element transducer comprising a plurality of component transducers, wherein at least one component transducer is driven by at least two driving circuits.

3. The apparatus according to claim 1, wherein said controller is further configured to selectively control said at least two driving circuits such that the emission of two or more ultrasonic beams at least partially temporally overlaps.

4. The apparatus according to claim 1, wherein said controller is further configured to selectively control said at least two driving circuits such that the emission of two of more ultrasonic beams is temporally distinct.

5. The apparatus according to claim 1, wherein said at least two driving circuits each has a different one of the plurality of resonant frequencies which essentially match the harmonic resonant frequencies of said transducer.

6. The apparatus according to claim 1, wherein: said controller is configured to selectively control said at least two driving circuits, such that said transducer is excited at least at a first and a third harmonic of the plurality of odd harmonic resonant frequencies of vibration; and the ultrasonic beam which induces cavitation in the adipose tissue is of the third harmonic, and the ultrasonic beam which slows down the rate of decrease in the amount of cavitation is of the first harmonic.

7. The apparatus according to claim 6, wherein the first harmonic is approximately 200 KHz and the third harmonic is approximately 680 KHz.

8. A method for lysing adipose tissue, the method comprising:
positioning a single element focusing piezoelectric transducer having a plurality of odd harmonic resonant frequencies of vibration, such that a focal region of the transducer is located inside the adipose tissue; and
automatically selectively controlling at least two circuits connected to the focusing piezoelectric transducer, thereby causing the transducer to vibrate at two or more of the plurality of odd harmonic resonant frequencies and to emit two or more ultrasonic beams, respectively, which at least partially overlap at the focal region, wherein at least one of the ultrasonic beams induces cavitation in the adipose tissue at the focal region, and a different at least one of the ultrasonic beams slows down the rate of decrease in the amount of cavitation.

9. The method according to claim 8, wherein:
causing the transducer to vibrate at two or more of the plurality of odd harmonic resonant frequencies comprises causing the transducer to vibrate at a first harmonic and at a third harmonic; and the third harmonic induces the cavitation in the adipose tissue and the first harmonic slows down the rate of decrease in the amount of cavitation.

10. The method according to claim 9, wherein the first harmonic is approximately 200 KHz and the third harmonic is approximately 680 KHz.

11. The method according to claim 8, wherein the cavitation comprises inertial cavitation.

12. The method according to claim 8, wherein the cavitation comprises non-inertial cavitation.

13. The method according to claim 8, wherein the automatic selective electrification is performed at two at least partially overlapping periods of time.

14. The method according to claim 8, wherein the automatic selective electrification is performed at two distinct periods of time.

15. An apparatus for lysing adipose tissue, the apparatus comprising:
a controller;
at least two driving circuits; and
a single element focusing piezoelectric transducer, wherein the controller and focusing piezoelectric transducer are connected to the at least two driving circuits and the controller is configured to selectively control the circuits, such that the transducer is excited at a plurality of odd harmonic resonant frequencies of vibration, the plurality comprising a first harmonic and a third harmonic, thereby emitting a plurality of ultrasonic beams that at least partially overlap at a focal region in the adipose tissue, and
wherein the ultrasonic beam of the third harmonic of the plurality of ultrasonic beams induces cavitation in the adipose tissue at the focal region and the ultrasonic beam of the first harmonic slows down the rate of decrease in the amount of cavitation, the first harmonic being approximately 200 KHz and the third harmonic being approximately 680 KHz.

* * * * *